United States Patent [19]
Andersen

[11] Patent Number: 5,234,457
[45] Date of Patent: Aug. 10, 1993

[54] IMPREGNATED STENT

[75] Inventor: Erik Andersen, Roskilde, Denmark

[73] Assignee: Boston Scientific Corporation, Watertown, Mass.

[21] Appl. No.: 773,847

[22] Filed: Oct. 9, 1991

[51] Int. Cl.$^5$ .................................... A61M 29/00
[52] U.S. Cl. ............................ 606/198; 606/108; 606/154; 606/195
[58] Field of Search ............... 606/108, 192, 194, 195, 606/198, 230, 77, 154, 191, 200; 623/1

[56] References Cited

U.S. PATENT DOCUMENTS

| | | | |
|---|---|---|---|
| 3,868,956 | 3/1975 | Alfidi et al. | 128/345 |
| 4,512,338 | 4/1985 | Balko et al. | 128/1 R |
| 4,580,568 | 4/1986 | Gianturco | 128/345 |
| 4,629,459 | 12/1986 | Ionescu et al. | 623/900 |
| 4,655,771 | 4/1987 | Wallsten | 623/1 |
| 4,665,918 | 5/1987 | Garza et al. | 128/343 |
| 4,690,684 | 9/1987 | McGreevy et al. | 623/12 |
| 4,733,665 | 3/1988 | Palmaz | 128/343 |
| 4,799,479 | 1/1989 | Spears | 128/303 |
| 4,878,906 | 11/1989 | Lindemann et al. | 606/155 |
| 4,913,141 | 4/1990 | Hillstead | 606/108 |
| 4,922,905 | 5/1990 | Strecker | 606/195 |
| 4,950,227 | 8/1990 | Savin | 606/192 |
| 5,026,377 | 6/1991 | Burton et al. | 606/108 |
| 5,061,275 | 10/1991 | Wallsten et al. | 623/1 |
| 5,078,720 | 1/1992 | Burton et al. | 606/108 |
| 5,089,005 | 2/1992 | Harada | 606/192 |
| 5,092,877 | 3/1992 | Pinchuk | 623/1 |
| 5,133,732 | 7/1992 | Wiktor | 606/195 |

FOREIGN PATENT DOCUMENTS 892980 4/1962 United Kingdom .................. 623/1

Primary Examiner—Edgar S. Burr
Assistant Examiner—Ren Yan
Attorney, Agent, or Firm—Pearson & Pearson

[57] ABSTRACT

A stent assembly, delivery system and method of manufacture therefor. A stent assembly includes a compact stent. A dissolvable material impregnates the stent in liquid form. In its cured, solid form, the material contains the stent in its compact form. When the stent is positioned in a vessel, the temperature and liquids in the vessel dissolve the material thereby to release the stent for positioning in a final configuration. The expansion of the stent then allows removal of the delivery system.

60 Claims, 5 Drawing Sheets

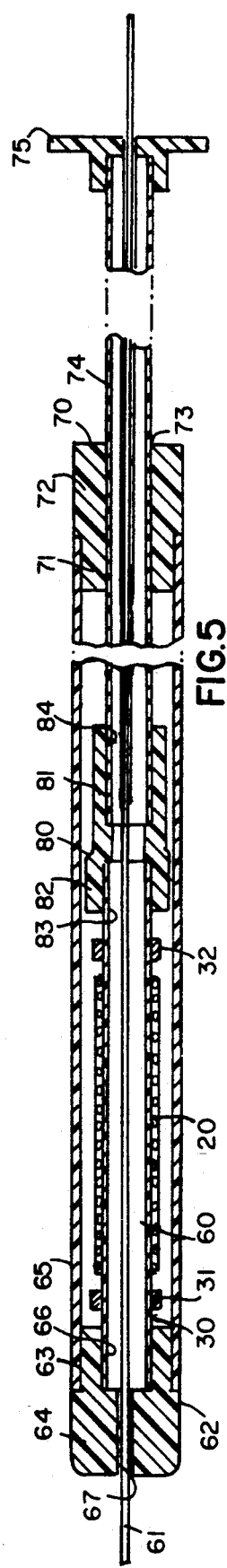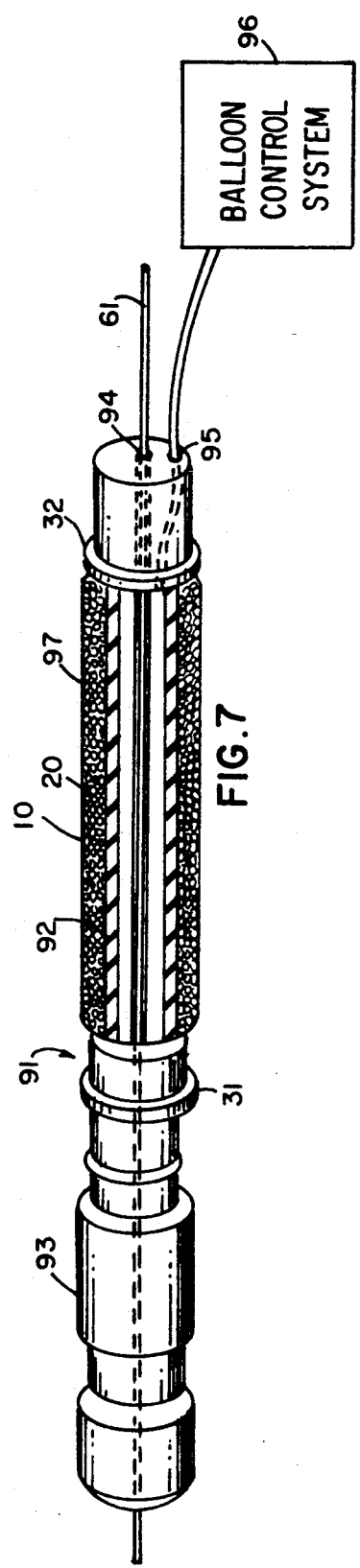

IMPREGNATED STENT

BACKGROUND OF THE INVENTION

1. Field of the Invention

This invention generally relates to a class of endoprostheses known as "stents" and more specifically to the structure and manufacture of such stents and the assembly of such stents into delivery systems.

2. Description of Related Art

Certain medical devices, called "stents", are well known and have a variety of forms. For example, U.S. Pat. No. 4,690,684 of Sep. 1, 1987 to McGreevy et al for a "Meltable Stent for Anastomosis" discloses a solid stent formed of a biologically compatible material, such a frozen blood plasma or the like. According to the disclosure, a solid stent of this type may be inserted into opposed ends of a ruptured vessel to support the separated vessel walls while the ends are bonded together. The heat from the bonding operation and the body eventually melt the stent and clear the vessel.

A stent that constitutes an endoprosthesis usually comprises a tubular structure that expands radially to be implanted into the tissue surrounding a "vessel" thereby to maintain its patency. It is well known that stents may be utilized in body canals, blood vessels, ducts and other body passageways, and the term "vessel" is meant to include all such passageways. Generally speaking, a stent delivery system includes the stent and some means for positioning and fixing the stent in place. Typically, the stent delivery system includes a catheter that supports the stent in a compacted form for transport to a site of implantation. Means integral with or ancillary to the catheter then expand the stent radially into the vessel walls to be implanted at the selected site. After the catheter is removed, the stent retains an expanded shape to keep the vessel walls from closing.

Stent delivery systems must conform to several important criteria. First, it is important to keep the transverse dimension of the delivery system to a minimum, so the stent must be capable of compaction against a delivery device, such as a catheter. Second, the delivery system must facilitate the deployment of the stent into contact with the vessel walls once it is located in a body. Third, the stent delivery system must easily disengage from the stent after the stent is deployed. Fourth, the procedure for removing the delivery system from the body must be straightforward. Fifth, the delivery system must operate reliably.

U.S. Pat. No. 4,922,905 of Ernst P. Strecker for a "Dilatation Catheter" describes the manufacture, construction and use of such stents and is incorporated herein by reference. In the specific disclosure of the Strecker patent, the stent comprises a tubular structure that is knitted from metal or plastic filament in loosely interlocked loops. A stent delivery system from metal or includes a balloon catheter and a coaxial sheath. The balloon catheter supports the compacted stent during its transport to a site within the body. The sheath covers the stent to prevent premature stent expansion and to facilitate the transfer of the stent through various passages in the body. A physician properly locates the stent, and then moves the sheath axially with respect to the catheter thereby to expose the stent. Then the physician operates a balloon pumping system to expand the balloon catheter and move the stent into a final configuration in contact with tissue surrounding the stent. When the stent expands radially, the filament material undergoes a plastic deformation. Consequently, the stent retains its new expanded shape. When the balloon subsequently deflates, it is free of the expanded stent, so the catheter, sheath and remainder of the delivery system can be withdrawn from the patient.

Commercial embodiments of the structures shown in the Strecker patent include rings for overlapping the end portions of the compacted stent thereby to eliminate the sheath. In such embodiments, however, the entire assembly of the catheter and compacted stent slides into position after passing through a previously positioned introducer sheath.

U.S. Pat. No. 4,733,665 of Mar. 29, 1988 to Palmaz for an "Expandable Intraluminal Graft, and Method and Apparatus for Implanting an Expandable Interluminal Graft" discloses a catheter with rings for positioning a compacted stent on a balloon portion of the catheter. A sleeve encases the compact stent. When the stent is properly positioned, a physician retracts the sleeve and pumps the catheter to expand the stent into position. During its expansion the stent detaches from the mounting rings. Then the physician deflates the balloon and removes the catheter, leaving the stent in place.

Other patents disclose other devices and operators for releasing stents. For example, in some stents the compaction process introduces stresses into the stent materials that act to expand the stent after its release from a sleeve or similar restraint. The following patents disclose examples of such structures:

U.S. Pat. No. 4,580,568 (1986) Gianturco
U.S. Pat. No. 4,665,918 (1987) Garza et al
U.S. Pat. No. 4,913,141 (1990) Hillstead Other patents disclose various structures in which heat expands the stent and include:

U.S. Pat. No. 3,868,956 (1975) Alfidi et al
U.S. Pat. No. 4,512,338 (1985) Balko et al
U.S. Pat. No. 4,799,479 (1989) Spears
U.S. Pat. No. 5,026,377 of Jun. 25, 1991 to Burton et al for a "Stent Placement Instrument and Method" discloses a delivery system for a self-expanding stent. The stent is a braided structure formed of a shape memory material. An outer sleeve retains the stent radially during transport to a final site within the body. A grip member enables both deployment and retraction of the stent. There are several examples of grip members in this patent. One, for example, comprises a releasable adhesive on a support for the stent. The adhesive grips the stent without slipping while the stent is in the instrument, but allows the stent to expand when a outer sleeve is retracted.

As known the overall diameter and flexibility of a stent and its delivery system determine the range of vessels that can receive a stent. It is important that any stent structure have as small an overall diameter as possible. The smaller the diameter, the greater the range of vessels for which the endoprosthesis becomes viable. That range of vessels is limited with prior art structures particularly by a protective sheath or the like that surrounds a stent and has two functions. First, the protective sheath provides a smooth surface over the stent to facilitate its transport through the body with minimal trauma. Second, the protective sheath prevents the stent from expanding prematurely. The second function determines the wall thickness of a sheath or like structure and with it the overall diameter of the stent delivery system. The wall must be sufficiently thick to provide the strength necessary to restrain the stent. This thickness is greater than the wall thickness required by the first function. For a given diameter stent, the overall diameter of the stent and the sheath or the like can exceed a minimal diameter. It is this characteristic that prevents the introduction of prior art stents into smaller vessels.

SUMMARY

Therefore it is an object of this invention to provide an improved stent system.

Another object of this invention is to provide an improved stent structure that minimizes the overall diameter of the stent and the apparatus for delivering the stent to a vessel.

Still another object of this invention is to provide an improved stent structure that is formed of a self-expending filament material in loosely interlocked loops.

Yet another object of this invention is to provide an improved stent structure that enables the placement of the stent in vessels that are smaller than those that could receive prior art stents.

Still another object of this invention is to provide a stent delivery system with an improved stent structure.

Still yet another object of this invention is to provide a stent delivery system with an improved stent structure that minimizes the overall diameter of the delivery system at the stent.

Yet still another object of this invention is to provide an improved stent delivery system with a stent that enables the placement of a stent in vessels that are smaller than those that could receive prior art stents.

Yet another object of this invention is to provide an improved method for the manufacture of stents.

Yet still another object of this invention is to provide an improved method for manufacture of stents that allows the incorporation of the stents in apparatus that is adapted for implanting the stent in smaller vessels than previously possible.

In accordance with this invention, the above objects are attained by a stent assembly that comprises a compact mesh in a cylindrical form. The mesh can expand into a cylindrical mesh stent that engages the tissue walls surrounding a vessel. A cured dissolvable material impregnates the mesh and contains the mesh in its compact form during placement. The cured material dissolves when the stent is in position in the body thereby to free the mesh and enable its expansion into a final form contacting the tissue surrounding the vessel.

In accordance with another aspect of this invention, a stent delivery system comprises an elongated stent assembly, a delivery structure for positioning the stent assembly at a predetermined position in the body and a stent support. The stent support is coaxial and coextensive with the stent assembly and affixes it to the delivery structure. The stent assembly includes a compact mesh and a cured soluble dissolvable material that impregnates and contains the mesh. After the stent assembly is properly positioned, the cured material, that is soluble in the vessel, dissolves and frees the mesh for expansion.

In still another aspect of this invention the manufacture of a stent assembly includes the step of producing a cylindrical stent in compact form. Then the stent is impregnated with dissolvable material in liquid form. The material cures and forms a solid structure for containing the stent in its compact form.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

FIG. 5 is a cross-sectional view of one embodiment of a stent delivery system constructed in accordance with this invention;

FIG. 7 is another embodiment of a stent delivery system constructed in accordance with this invention.

DESCRIPTION OF ILLUSTRATIVE EMBODIMENTS

Figure 1:
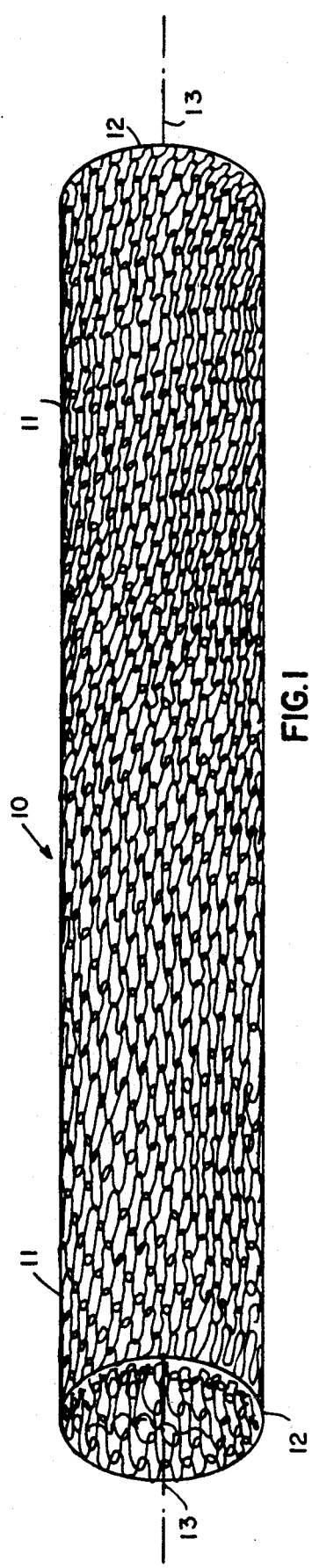
FIG. 1 depicts a stent that is adapted for use in connection with this invention.

FIG. 1 discloses one embodiment of a tubular endoprothesis stent 10, in expanded form and constructed in accordance with the disclosure of the previously identified U.S. Pat. No. 4,922,905. In this particular embodiment the stent 10 comprises a single filament 11 that is knitted into a mesh cylinder 12 extending coaxially with an axis 13 and comprising a fabric of loosely interlocked filament loops that form the wall of the cylinder 12. The filament can be selected from two groups of materials depending upon the ultimate characteristics of the stent 10.

Generally, the filament 11 should be formed of a biocompatible material. When expanded to a final form as shown in FIG. 1, the structure should be resistant to subsequent deformation. Thus these materials normally are taken from a group of shape memory metals that maintain the stent in an expanded form. The material preferably is radiopaque.

When a stent 10 is to be self-expanding, a self-expanding material such as a super elastic material is selected so compaction produces internal restoring forces within the material. Nitinol is an example of such a super elastic material that is particularly adapted for self-expanding stents. Obviously if the stent 10 is self-expanding, it will be necessary to contain such self-expanding stents in compact form. The stent 10 will return to the shape shown in FIG. 1 when it is freed from any containment.

If some external apparatus, such as a balloon catheter, is to expand the stent 10, the stent 10 may be comprised of a material from a group of plastic deformable materials that include stainless steel and tantalum.

Figure 2:
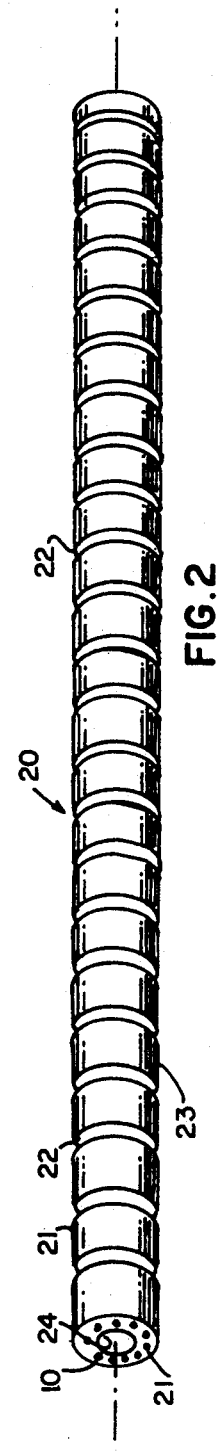
FIG. 2 depicts a stent assembly embodying this invention.

In accordance with another aspect of this invention, the stent 10 in FIG. 1 is compacted into a stent assembly 20 as shown in FIG. 2. As described in more detail later, compaction can produce a reduction in the overall radius of the stent 10 by a 10:1 with about a 30% increase in the overall length of the stent 10. The stent assembly 20 also includes a cured, dissolvable material that readily shifts between liquid and solid phases at a melting temperature in the range of 30° C. to 40° C. This material impregnates the interstices of the mesh stent 10 and has sufficient strength to contain the stent 10 in its compact form.

There are several materials that have these characteristics, including polymers, such as resorbable polyesters or polyvinyl alcohol based materials and gelatin. Gelatin is particularly adapted for use in accordance with this invention as it transforms from a liquid form on cooling into a cured, solid mass. The mass has sufficient strength to contain the stent 10 in its compact form, even when the stent 10 is formed of a self expanding material. Gelatin also has the property of liquefying when heated above some predetermined temperature that is normally less than 37° C. In addition certain enzymes, such as those found in the body, will attack the gelatin and cause it to lose its strength and viscosity.

Thus, when a stent assembly 20 having a compact stent 10 and gelatin 21 as shown in FIG. 2 is introduced into the body, the body temperature and liquids that the stent assembly 20 contacts coact to liquify the gelatin. The body fluids transport the gelatin out of the system and this liquefaction releases the stent for expansion.

The rate of thermal decomposition of gelatin depends upon the type and quality of the gelatin, the temperature of the gelatin and the nature of any enzymes that may attack the solution. All these parameters can be controlled by the selection of gelatins with particular properties. Particularly, it has been found that Vee Gee Extra Fine 100 Bloom Type A gelatin or Vee Gee 100 Bloom Type B gelatin from the Vyse Gelatin Company produce satisfactory gelatins for impregnating a mesh stent.

Although the stent assembly 20 may be constructed with pure gelatin or like dissolvable materials that only contain the stent, other disparate constituents can be added for producing other functions. For example, it is possible to mix barium or other marker materials into gelatin for assisting during fluoroscopy or other imaging techniques. Alternatively the gelatin or other material could entrain any of a number of encapsulated medicines for a timed release into the body as the material dissolves, particularly if a gelatin is designed to dissolve over a longer time period. It is also possible to combine the markers or medicines in a stent assembly comprising an axial distribution of gelatins or other materials with different rates of thermal decomposition. In such an application, the materials would release at differing times and rates. Moreover, the axial distribution could be used to control the physical profile of a the stent as it expands.

When a stent is impregnated with a cured gelatin or other material, it becomes rigid. This rigidity impacts the ability of the stent assembly 20 to pass through a tortious path to a vessel. In accordance with another aspect of this invention, a helical groove 22 in the outer cylindrical surface 23 of the stent assembly 20 facilitates bending of the stent assembly 20. As another alternative, the gelatin 21 could be located at discrete, separated axial positions along the length of the compact stent and achieve the same general results while also improving flexibility. As still another alternative a groove could be formed on an inner cylindrical surface 24 of the stent assembly 20.

The exact method of manufacture of a given stent assembly in accordance with this invention depends upon several factors. Two major factors are the final application for the stent and whether the stent 10 is formed of a self-expanding material or an expansible material that requires some external force to expand it.

Figure 3A:
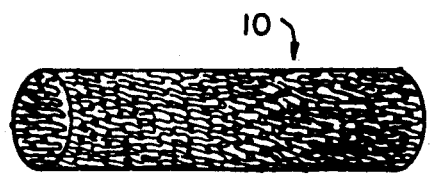
FIG. 3 including FIGS. 3A through 3F and FIG. 4, taken together, depict manufacturing steps that convert the stent of FIG. 1 to a stent assembly as shown in FIG. 2.
Figure 4:
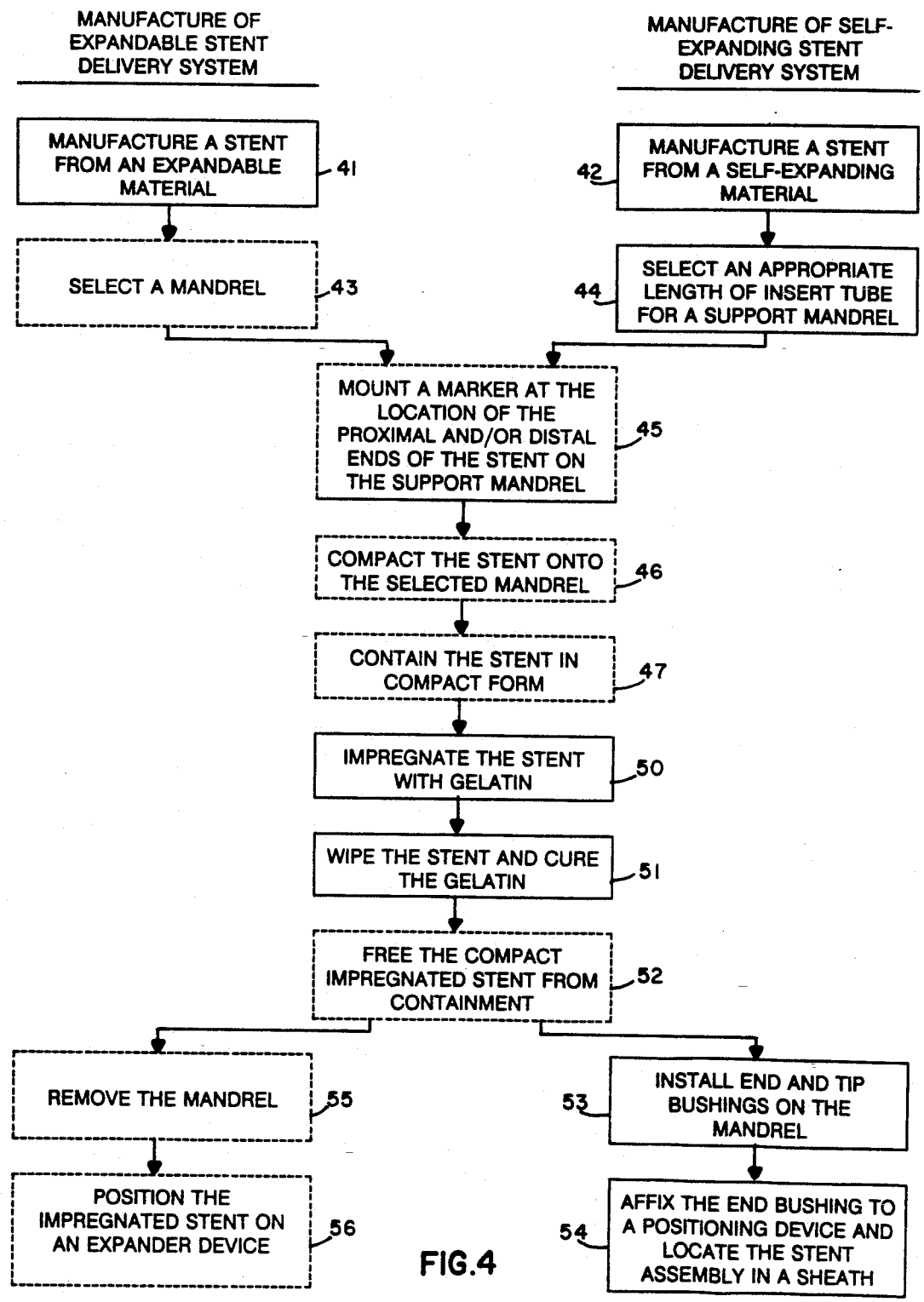

The manufacturing process begins with a selection of a stent 10 shown in FIG. 3A and represented by steps 41 and 42 in FIG. 4. That is, in accordance with step 41 the stent 10 in FIG. 3A would be formed of an expansible plastic deformable material, such as stainless steel or tantalum. In step 42 the stent would be selected from any of the self-expanding super elastic alloys for stent material such as Nitinol.

Figure 3B:
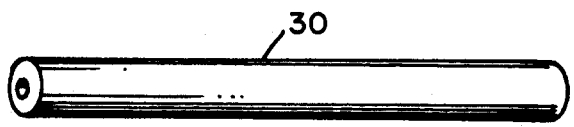

A next step is optional and dependent upon the end application. As shown by step 43, it is possible to select a mandrel 30 in FIG. 3B. If the stent 10 is already in a compact form, it may be possible that no mandrel is required at all. In other applications, the mandrel 30 might become an integral part of the final stent assembly 20. In such an application the mandrel might constitute a balloon portion of a balloon catheter. In still other applications, the mandrel 30 might be used only for manufacture and then removed from the final stent assembly 20. If the stent is to be manufactured as a self-expanding stent, the mandrel 30 might be selected as a tube insert formed of an extruded polymer material as shown in step 44.

Figure 3C:
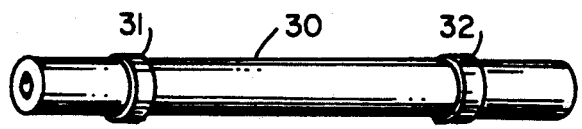

Step 45 in FIG. 4, is also an optional step in which radiopaque markers 31 and 32 are attached to the mandrel 30, as shown in FIG. 3C. The spacing between the markers 31 and 32 corresponds to the axial length of the stent 10 of FIG. 3A in its compact form.

Figure 3D:
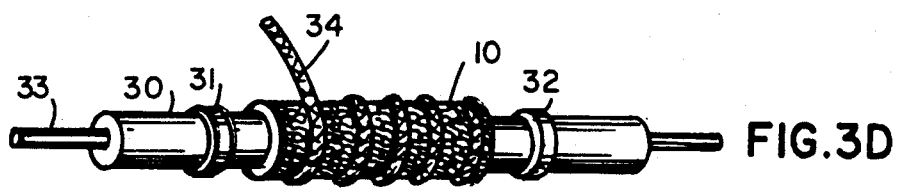
Figure 3E:
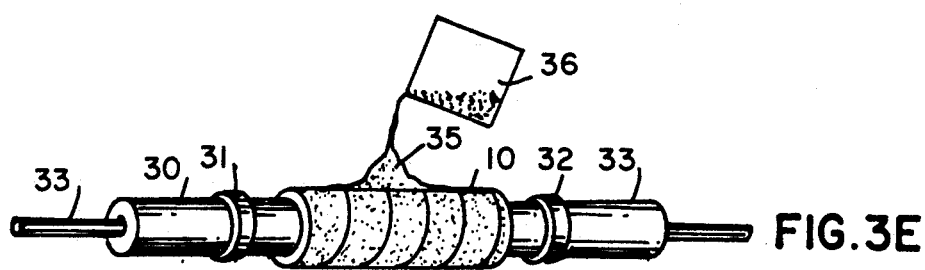

In step 46 the stent 10, if in an expanded form, is compacted onto the mandrel 30 by applying tension in an axial direction simultaneously with radial compression so the stent will have a low profile that facilitates its introduction into a body passageway. During this process, as shown in FIG. 3D, a supplementary mandrel 33 can be positioned in the mandrel 30 for added support. During the compaction process, a filament 34 may be wrapped around the compacted stent 10 and tied to the mandrel 30 in step 47. This filament 34 contains the stent 10 in its compact form for subsequent processing. The filament 34 can comprise any number of materials that contain the stent in its compact form during the processing and do not adhere to the gelatin or other material that impregnates the stent. Elastic filaments containing polymeric silicons are preferred because of advantages in subsequent processing steps; Silastic ® filaments are examples.

In step 50, liquid gelatin 35, or a similar liquid, is poured from a container 36 onto the stent 10 while the entire assembly rotates on the mandrel 33. The liquid 35 fills the spaces formed by the interstices of the mesh and the spaces between the filament 34. As the material 35 fills the interstices of the compact stent 10, it cools and begins to form a semi-rigid mass.

Figure 3F:
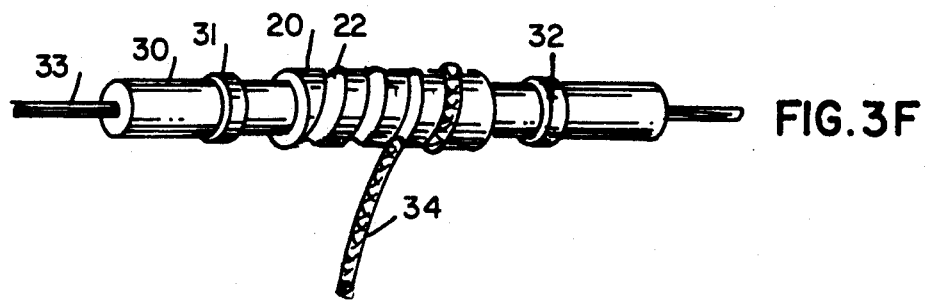

In step 51 excess material 35 is wiped from the stent 10 and the material 35 cures to produce an interdisposed restraining structure for maintaining the stent in its compact form. After the material 35 cures, it is possible to remove the filament 34 from the assembly. If this is an elastic material, then applying tension to the filament 34 reduces its diameter slightly and facilitates its removal from the cured material 35. This leaves the helical groove 22 shown in FIG. 3F that improves the overall flexibility of the stent assembly 20. The stent 10 remains in a compact form because the cured dissolvable material 35, such as cured gelatin, has sufficient strength to contain the stent 10.

If the stent assembly 10 is being manufactured of a self-expanding material, the procedure may then use step 53 to install various termination elements, such as end and tip bushings, as needed on the mandrel 30, and step 54 to affix a positioning, or steering device in the end bushing and to locate the stent assembly in a sheath. During the manufacture of a stent assembly 20 that relies on some external means for expansion, optional step 55 is used to remove the mandrel 30 if that mandrel is not required in the final assembly. If that mandrel is formed of a Silastic material, its removal is facilitated as tensioning the material in an axial direction reduces its diameter and facilitates its removal from a central aperture along the axis of the assembly. In that case the structure that results from the manufacture appears as the structure in FIG. 2 that is adapted for later installation on an expansion or other device. Step 56 represents procedures for finally positioning the stent assembly 20 on a support device.

FIG. 5 discloses an embodiment of a stent delivery system that is adapted for positioning a self-expanding stent assembly in a vessel. As previously indicated with respect to steps 53 and 54, the impregnated stent assembly 20 mounts on a tubular mandrel 30 with markers 31 and 32. A central aperture 60 through the tubular mandrel 30 enables the tube to slide over a guide wire 61. A tip bushing 62 includes a hollow shank portion 63 and an end portion 64. The shank portion 63 has an outer diameter that interfits with a distal end of a sheath 65 and a center aperture 66 that fits snugly over the tubular mandrel 30. A central aperture 67 in the tip 61 aligns with the central aperture 60 thereby to allow the guide wire 61 to pass through the tip 62.

The proximal end of the sheath 65 terminates at a steering bushing 70 that includes a shank portion 71 that receives the proximal end of the sheath 65 and a head portion 72. The steering bushing 70 has a central aperture or through hole 73 that allows the passage of a pusher tube 74 therethrough. At its proximal end, the pusher tube 74 terminates in a handle or thumb pad 75.

At its distal end, the tube 74 engages an end bushing 80. The end bushing 80 has a proximal shank portion 81 and a distal head portion 82. An aperture 83 is coextensive with at least the head portion 82 and receives the proximal end of the mandrel 30. The shank portion 81 has another aperture 84 that receives the distal end of the pusher tube 74. The diameter of the head portion 82 is selected so it can slide freely within the sheath 65.

Figure 6:
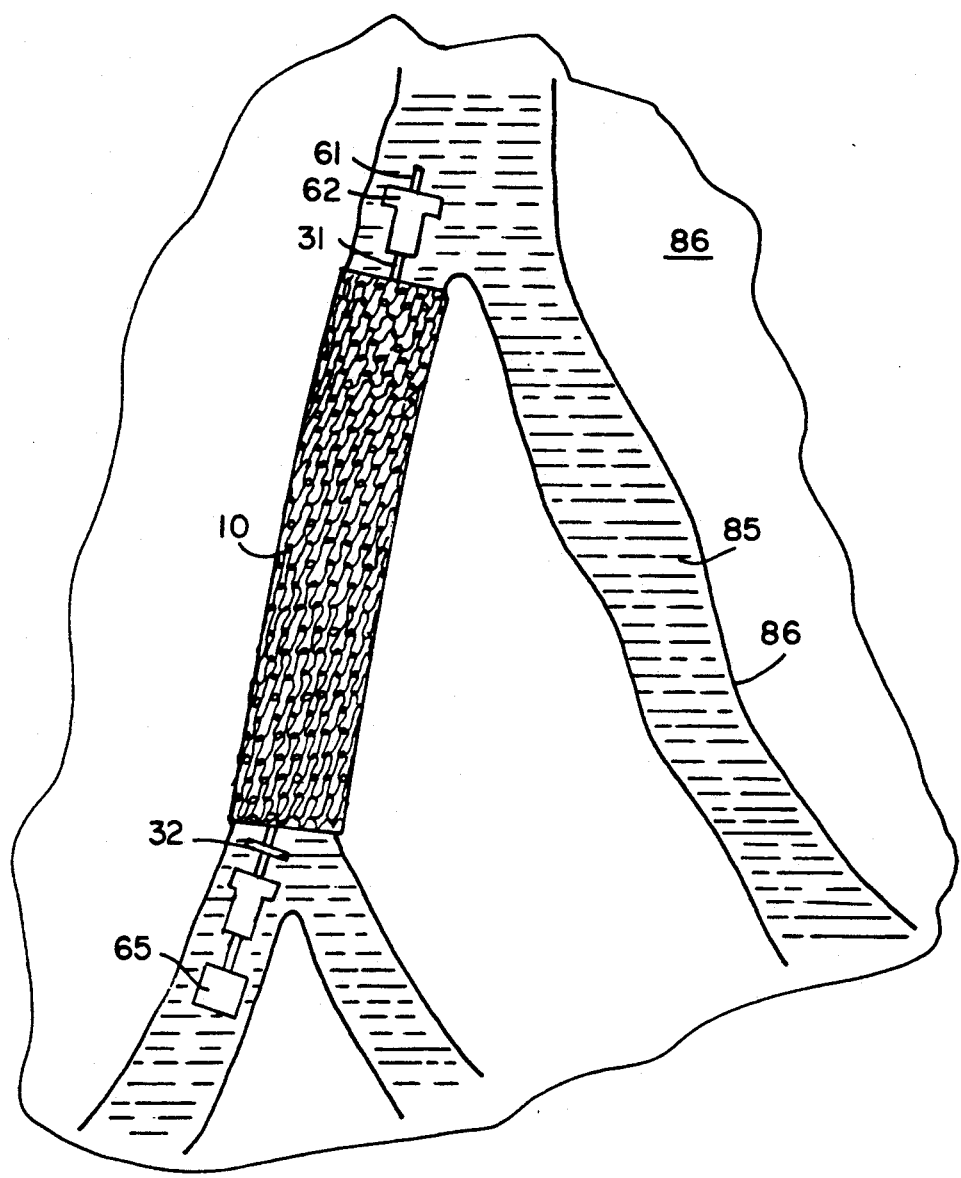
FIG. 6 is a view of a vessel with a stent and a stent delivery system of FIG. 5 positioned therein.

In use the guide wire 61 will be located in a body as shown in FIGS. 5 and 6. Then the assembly, shown in FIG. 5, can be slid over the guide wire 61. During transport the tip bushing 62 seals the end of the stent delivery system and prevents any body fluids 84 from reaching the stent assembly 20 as the stent assembly passes through various vessels 85 in tissue 86. Radiographic or fluoroscopic techniques provide final location information by imaging the markers 31 and 32. The physician can then withdraw the steering bushing 70 toward the pusher tube 74 thereby withdrawing the sheath 65 from the tip bushing 62. This exposes the stent assembly 20 to the body fluids. The fluids, through their temperature and constituents, dissolve the material 21, such as gelatin, over a controlled time interval. As the gelatin dissolves, and shifts from a solid phase to a liquid phase the body fluids flush the gelatin material, now in the liquid phase, from the site and the stent 10 eventually expands into a final form as shown in FIG. 6. When this occurs, the stent 10 has a much larger diameter than the overall diameter of the stent delivery system including the tip bushing 62, so the entire stent delivery system can be withdrawn along the guide wire 61 and removed from the body.

FIG. 7 depicts an embodiment in which a balloon catheter 91 supports a stent assembly 20 as an example of a stent that requires an external force to expand. In this particular embodiment a balloon 92 could constitute a mandrel 30 in FIG. 3B to support the stent assembly 20. The remaining portions of the balloon catheter include a central supporting catheter 93 typically with two lumens. A central lumen 94 receives a guide wire 61. A second lumen 95 provides a passage for allowing a balloon control system 96 to inflate and deflate the balloon 92. FIG. 7 also includes the markers 31 and 32 at the opposite ends of the stent assembly 20.

The delivery system in FIG. 7 may or may not be constructed with a protective sheath. If the dissolvable material is selected properly, it is possible to introduce the stent assembly into the body without any protective sheath. In such an embodiment, the body fluids and the temperature will produce slow initial dissolution at the circumferential surface 97 of the stent 20. This surface is relatively smooth and the slight melting produces a lubricating function thereby to allow the structure to transfer through the vessels with minimal trauma.

Once the stent is located in a final position, a sheath, if used, is withdrawn. When the gelatin dissolves, the stent 10 will be freed from the balloon catheter and pumping the balloon catheter expands the balloon 92 thereby forcing the stent 10 into its final position. After this occurs, the balloon control system 96 deflates the balloon 92 and the entire balloon catheter 91 can be withdrawn along the guide wire 61.

In summary, this invention provides an improved stent assembly that uses a cured, dissolvable material to retain a stent in a compact form until it is properly oriented within a vessel. Specific materials for containing the stent are disclosed. Others may also exist or be developed that will shift from a liquid state to a solid state at room temperature and shift back to a liquid state at a controlled rate at temperatures normally encountered in the body. The same material can be utilized with both self-expanding stents and stents that require some external source for expansion.

A stent may be formed in compact form or be compacted from a final form. Different stents can comprise a wide variety of materials or combinations of materials. The stents may be knitted, woven, formed, rolled, extruded or machined. The term "mesh" is exemplary only. Some delivery systems may include external sheaths around the stent assembly; others may not. When a sheath is desirable, the sheath can be very thin because it only needs to provide a smooth exterior surface. There is no requirement for the sheath having sufficient strength to contain a stent. As a result, the overall size of a stent delivery system decreases so it can transfer a stent assembly into smaller vessels. Other configurations of catheters and delivery systems could be substituted for either self-expanding stents or stents requiring some external expansion source.

Although this stent assembly has been described in terms of particular cured dissolvable materials, stent materials and two specific stent delivery systems, it will be apparent that many modifications can be made with the attainment of some or all of the objects and advantages of this invention. Moreover it will be apparent that many modifications can be made to the disclosed apparatus without departing from the invention. Therefore, it is the intent of the appended claims to cover all such variations and modifications as come within the true spirit and scope of this invention.

What is claimed as new and desired to be secured by Letters Patent of the United States is:

1. A stent assembly for insertion in a vessel bounded by a vessel wall comprising:
   A. compact mesh stent means in a cylindrical form for expanding into engagement with a vessel wall, and
   B. cured, dissolvable means impregnating said mesh for containing said mesh in its compact form, said cured, dissolvable means transforming from a solid to a liquid state when said stent assembly is in position in the vessel thereby to free said stent and enable its expansion into a vessel wall.

2. A stent assembly as recited in claim 1 wherein said stent means consists of a filament formed of a biocompatible material that resists deformation in an expanded form.

3. A stent assembly as recited in claim 1 wherein said stent assembly is disposed along a longitudinal axis and additionally comprises central support mean at the interior of said stent assembly that is concentric with the axis.

4. A stent assembly as recited in claim 3 wherein said central support means includes means for expanding said mesh stent into its final expanded form.

5. A stent assembly as recited in claim 1 wherein said cured, dissolvable means in said stent assembly comprises discrete axial segments for improving the flexibility of said stent assembly.

6. A stent assembly as recited in claim 5 wherein a cylindrical surface of said cured, dissolvable means has a helical groove formed therein for producing said axial segments.

7. A stent assembly as recited in claim 1 wherein said dissolvable means additionally entrains a disparate constituent for release into the vessel as said dissolvable means dissolves.

8. A stent assembly as recited in claim 1 wherein said dissolvable means comprises gelatin.

9. A stent assembly as recited in claim 8 wherein said mesh stent means is formed of a material taken from the group of materials consisting of super elastic alloys and plastic deformable alloys.

10. A stent assembly as recited in claim 8 wherein said mesh stent means is formed of Nitinol.

11. A stent assembly as recited in claim 10 wherein said cured, dissolvable means forms a cylinder and said stent assembly additionally comprises a central coaxial support for said cylindrical cured, dissolvable means.

12. A stent assembly as recited in claim 10 wherein said stent means is formed of a material taken from a group consisting of stainless steel and tantalum.

13. A stent assembly as recited in claim 12 wherein said cured, dissolvable means forms a cylinder and said stent assembly additionally comprises a central coaxial support for said cylindrical cured, dissolvable means, said central coaxial support means includes means for expanding said mesh stent into its final expanded form.

14. A stent delivery system for positioning a stent in a vessel having a defining vessel wall and comprising:
   A. an elongated stent including mesh means including a cylindrical mesh stent for expanding from a compact form to an expanded form to engage the vessel wall and a cured, dissolvable means that impregnates said mesh means for containing said mesh means in its compact state,
   B. delivery means for positioning said stent at a predetermined position in the vessel, and
   C. stent support means coaxial and coextensive with said stent means for affixing said stent means to said delivery means, said cured, dissolvable means being soluble in the vessel thereby to dissolve and free said mesh means for expansion into the vessel wall.

15. A stent delivery system as recited in claim 14 wherein said compact mesh means is formed by a filament taken from the group of materials consisting of shape memory materials including Nitinol and of super elastic alloys including stainless steel and tantulum.

16. A stent delivery system as recited in claim 15 wherein said stent has a cylindrical shape extending along an axis and said stent support means comprises a coaxial tube means for contacting the inner cylindrical surface of said stent and distal tip means and proximal bushing means mounted to said coaxial tube means at the distal and proximal ends of said stent means respectively for preventing axial motion of said stent relative to said coaxial tube means.

17. A stent delivery system as recited in claim 16 wherein said delivery means includes:
   i. cylindrical sheath means for overlying said stent and said stent support means, and
   ii. steering means connected to said proximal bushing means for moving said sheath means and contained stent means to a predetermined position in the body canal, said delivery means including means for moving said sheath means relative to said steering means to withdraw said sheath from said stent thereby to enable said cured, dissolvable means to dissolve and said mesh means to expand into contact with the body canal.

18. A stent delivery system as recited in claim 17 wherein said distal tip means includes means for sealing against said sheath means thereby to prevent fluid from contacting said cured, dissolvable means during the positioning of said stent.

19. A stent delivery system as recited in claim 15 wherein said stent comprise a mesh formed of Nitinol.

20. A stent delivery system as recited in claim 14 wherein said mesh means is formed of a plastic deformable material and said stent support means includes expansion means for expanding said mesh means into the body canal after said cured, dissolvable means dissolves.

21. A stent delivery system as recited in claim 20 wherein said expansion means comprises balloon catheter means.

22. A stent delivery system as recited in claim 21 wherein said stent delivery system additionally comprises means for inflating said balloon catheter to position said mesh means against the vessel wall and for deflating said balloon catheter thereby to separate said mesh means and said catheter and to enable the removal of said delivery system from the vessel.

23. A stent delivery system as recited in claim 14 for use with a guide wire wherein each of said delivery means and stent support means have a common axial passage therethrough for allowing said delivery means to be positioned along the guide wire.

24. A stent delivery system as recited in claim 14 wherein said cured, dissolvable means in said stent assembly comprises discrete axial segments for improving the flexibility of said stent assembly.

25. A stent delivery system as recited in claim 24 wherein a cylindrical surface of said cured, dissolvable means has a helical groove formed therein for producing said axial segments.

26. A stent delivery system as recited in claim 14 wherein said cured, dissolvable means additionally includes an entrained disparate material that dissolves in the body as it is released as said dissolvable means dissolves.

27. A stent delivery system as recited in claim 14 wherein said stent support means includes marker means for enabling a determination of the location of the stent support means within a vessel.

28. A method for making a stent assembly comprising the steps of:
A. producing a cylindrical stent in a compact form,
B. impregnating the stent a dissolvable substance in liquid form while the stent is in its compact form, and
C. curing the dissolvable substance thereby to form a solid retaining structure for maintaining the stent in the compact form, the substance decomposing in the environment of a body.

29. A method for making a stent assembly as recited in claim 28 wherein said producing step includes wrapping a filament about the compact stent, said filament being formed of a material that does not bond with the dissolvable substance as it cures.

30. A method for making a stent assembly as recited in claim 29 wherein said impregnation of the stent is produced by dipping the compact stent into the dissolvable substance in a liquid state and thereafter removing excess dissolvable substance.

31. A method for making a stent assembly as recited in claim 29 wherein said impregnation of the stent is produced by rotating the compact stent and by pouring the dissolvable substance in a liquid state onto the stent and thereafter by removing excess dissolvable substance.

32. A method for making a stent assembly as recited in claim 29 wherein said producing step includes positioning the stent form on a mandrel and wrapping spaced turns of a filament about the compact stent and affixing the ends of the filament to the mandrel at the axial ends of the compact stent, said method including the additional step of removing the filament from the stent after said curing step thereby to form a continuous groove in the surface of the cured, impregnated stent.

33. A method for making a stent assembly as recited in claim 29 wherein said producing step includes positioning the stent form on a mandrel and said wrapping step includes wrapping spaced turns of a filament comprises of an elastic material containing polymeric silicones about the compact stent and affixing the ends of the filament to the mandrel at the opposite ends of the compact stent, said method including the additional steps of stretching and removing the filament from the stent after said curing step is completed thereby to form a continuous groove in the surface of the cured, impregnated stent.

34. A method for making a stent assembly as recited in claim 29 wherein said method additionally includes mounting at least one marker to the compact stent thereby to enable the position of the stent to be determined in use.

35. A method for making a stent assembly as recited in claim 28 wherein said impregnation of the stent is produced by dipping the compact stent into the dissolvable substance in liquid form and thereafter removing excess amounts of the dissolvable substance.

36. A method for making a stent assembly as recited in claim 28 wherein said impregnation of the stent is produced by rotating the compact stent and by pouring the dissolvable substance in a liquid state onto the stent and thereafter by removing any excess amounts of the dissolvable substance.

37. A method for making a stent assembly as recited in claim 28 wherein said method additionally includes mounting at least one marker to the compact stent thereby to enable the position of the stent to be determined in use.

38. A method for making a stent assembly as recited in claim 28 wherein during the stent formation said stent is produced from a super elastic material whereby the stent is self-expanding when the cured dissolvable substance dissolves in use.

39. A method for making a stent assembly as recited in claim 38 wherein said method additionally comprises the step of mounting termination elements at each end of a mandrel after said curing step has completed.

40. A method for making a stent assembly as recited in claim 38 wherein said method additionally comprises the steps of mounting on a mandrel the cured, impregnated stent and termination elements in an open-ended sheath and affixing to one of the termination elements steering means for enabling the stent assembly and sheath to be positioned in use.

41. A method for making a stent assembly as recited in claim 28 wherein producing the stent includes the steps of forming a filament into the stent form whereby the stent form is expandable and positioning the stent form on a mandrel.

42. A method for making a stent assembly as recited in claim 41 wherein said filament formation step includes the manipulation of a filament composed of a plastic deformable material.

43. A method for making a stent assembly as recited in claim 41 wherein the mandrel is formed of an elastic material containing polymeric silicones and said method comprises the additional step of stretching and removing the mandrel from the cured, impregnated stent after said curing step is completed.

44. A method for making a stent assembly as recited in claim 41 wherein said stent positioning step includes the positioning of the stent on an expandable mandrel whereby the mandrel carries the stent in use and expands the stent after the dissolvable substance dissolves.

45. A tubular endoprothesis device for location in a vessel having a wall structure comprised of an open fabric of loosely interlocked loops of filament material, the device having a first relatively small diameter form for a low profile introduction into a body passageway, said interlocked loops being made from a self-expanding metallic alloy to permit radial self-expansion thereof in a vessel and dissolvable impregnating means impregnating said loops for restraining the wall structure in its small diameter form.

46. A tubular endoprothesis device as recited in claim 45 wherein said impregnating means comprises a cured dissolvable material which shifts from a solid phase to a liquid phase in a vessel thereby to release said wall structure for expansion.

47. A tubular endoprothesis for placement in a lumen defined by a wall body, said endoprothesis comprising a wall structure of loosely interlocked knitted loops of metal filament, said wall structure being radially compactible to a small radial size without deformation to produce an internal self-restoring force for introduction lengthwise into the lumen, said wall structure, when free, being radially self-expanding to tubular form to engage the wall of the lumen and a dissolvable polymer for impregnating said wall structure to contain said endoprothesis in its compacted configuration.

48. A tubular endoprothesis as recited in claim 47 wherein said metal filament is formed of a shape memory metal.

49. A tubular endoprothesis as recited in claim 47 wherein said metal filament comprises substantially nitinol.

50. A tubular endoprothesis as recited in claim 47 wherein the ratio of the radii of said tubular wall structure in its expanded and compacted forms is in the order 10:1.

51. A placement system for an endoprothesis in a lumen defined by a wall of a body comprising:
   A. an endoprothesis having tubular wall means of loosely interlocked knitted loops of metal filament, said wall being radially compactible to a small radial size without plastic deformation of the filament to produce an internal self-restoring force, and to facilitate the lengthwise introduction of said endoprothesis into the lumen, said wall means, when free, being radially self-expandable to tubular form to engage the wall of said lumen,
   B. means for placing said endoprothesis in the lumen, and
   C. dissolvable restraint means impregnating said knitted loops for maintaining said endoprothesis in its compacted form and for freeing said endoprothesis for self-expansion into engagement with the wall of the lumen at the site of placement within the body.

52. A placement system as recited in claim 51 wherein said filament is formed from a shape memory metal.

53. A placement system as recited in claim 51 wherein said filament comprises substantially nitinol.

54. A placement system as recited in claim 51 wherein the ratio of the radii of said tubular wall structure in its expanded and compacted forms is in the order 10:1.

55. A placement system as recited in claim 51 wherein said dissolvable restraint means comprises a dissolvable polymer.

56. A placement system as recited in claim 51 wherein said delivery system additionally includes a cylindrical sheath overlying said endoprothesis, said sheath being retractable to expose said endoprothesis and said dissolvable restraint means to the body lumen.

57. A placement system as recited in claim 56 wherein said filament is formed from a shape memory metal.

58. A placement system as recited in claim 56 wherein said filament comprises substantially nitinol.

59. A placement system as recited in claim 56 wherein the ratio of the radii of said tubular wall structure in its expanded and compacted forms is in the order 10:1.

60. A placement system as recited in claim 56 wherein said dissolvable restraint means includes a dissolvable polymer for maintaining said endoprothesis in its compacted configuration, the removal of said cylindrical sheath enabling said polymer to dissolve and thereby release said endoprothesis for self-expansion.

* * * * *

UNITED STATES PATENT AND TRADEMARK OFFICE
Certificate

Patent No. 5,234,457                                                      Patented: August 10, 1993

On petition requesting issuance of a certificate for correction of inventorship pursuant to 35 U.S.C. 256, it has been found that the above identified patent, through error and without deceptive intent, improperly sets forth the inventorship.

Accordingly, it is hereby certified that the correct inventorship of this patent is: Erik Andersen, Osted, Denmark; and Ernest P. Strecker, Karlsruhe, Germany.

Signed and Sealed this Nineteenth Day of May, 1998.

<div align="right">

EDGAR S. BURR, *SPE*
Art Unit 2854

</div>